United States Patent
MacIntyre et al.

(10) Patent No.: US 7,933,005 B2
(45) Date of Patent: *Apr. 26, 2011

(54) MODIFIED METHOD AND APPARATUS FOR MEASURING ANALYTES

(75) Inventors: Duncan MacIntyre, Campbellville (CA); Ash Kaushal, Mississauga (CA); Paul Endersby, Campbellville (CA)

(73) Assignee: NIR Diagnostics Inc., Campbellville, Ontario (CA)

( * ) Notice: Subject to any disclaimer, the term of this patent is extended or adjusted under 35 U.S.C. 154(b) by 892 days.

This patent is subject to a terminal disclaimer.

(21) Appl. No.: 11/562,306

(22) Filed: Nov. 21, 2006

(65) Prior Publication Data

US 2007/0177130 A1 Aug. 2, 2007

Related U.S. Application Data

(60) Provisional application No. 60/738,526, filed on Nov. 21, 2005.

(51) Int. Cl.
*G01N 33/48* (2006.01)
(52) U.S. Cl. ............................ 356/40; 356/39
(58) Field of Classification Search ............... 356/39–43
See application file for complete search history.

(56) References Cited

U.S. PATENT DOCUMENTS

| | | | |
|---|---|---|---|
| 4,387,972 A | 6/1983 | Valencia | |
| 4,791,938 A | 12/1988 | Van Valkenburg | |
| 5,059,394 A * | 10/1991 | Phillips et al. | 422/68.1 |
| 5,207,984 A | 5/1993 | Kheiri | |
| 5,361,758 A | 11/1994 | Hall | |
| 5,736,103 A * | 4/1998 | Pugh | 422/68.1 |
| 5,800,781 A | 9/1998 | Gavin | |
| 6,040,578 A | 3/2000 | Malin | |
| 6,055,060 A * | 4/2000 | Bolduan et al. | 356/433 |
| 6,099,484 A * | 8/2000 | Douglas et al. | 600/583 |
| 6,201,607 B1 * | 3/2001 | Roth et al. | 356/445 |
| 6,236,047 B1 | 5/2001 | Malin | |
| 6,353,471 B1 | 3/2002 | Samsoondar et al. | |
| 6,365,363 B1 | 4/2002 | Parfenov | |
| 6,430,513 B1 | 8/2002 | Wang et al. | |
| 6,448,067 B1 * | 9/2002 | Tajnafoi | 435/288.7 |
| 6,549,795 B1 | 4/2003 | Chance | |

(Continued)

FOREIGN PATENT DOCUMENTS

| | | |
|---|---|---|
| CA | 2475622 | 1/2005 |
| WO | WO 98/39634 | 9/1998 |
| WO | WO 99/47261 | 9/1999 |
| WO | WO 00/70350 | 11/2000 |
| WO | WO 2007028231 | 3/2007 |

OTHER PUBLICATIONS

Office Action dated Jun. 8, 2010 for U.S. Appl. No. 11/463,232, filed Aug. 8, 2006; Inventor: MacIntyre, Ducan (8 pages).

*Primary Examiner* — Michael P Stafira
(74) *Attorney, Agent, or Firm* — Hovey Williams LLP

(57) ABSTRACT

A device for measuring a compound with in a sample both non-invasively and invasively is provided. The devise comprised a source of electromagnetic radiation (EMR) operatively coupled to a power source, one or more receptors and a detector. The one or more receptors shaped to receive a body part and a sample holder and optically coupled to the source of EMR by one or more radiation guiding elements. The radiation guiding element comprising an input in operable association with the source of EMR, and an output in operable association with a detector and coupled to a processing system.

27 Claims, 10 Drawing Sheets

U.S. PATENT DOCUMENTS

| | | |
|---|---|---|
| 6,651,015 B2 | 11/2003 | Samsoondar |
| 6,741,876 B1 | 5/2004 | Scecina |
| 6,819,950 B2 | 11/2004 | Mills |
| 7,050,157 B2 * | 5/2006 | Braig et al. ............. 356/39 |
| 7,379,167 B2 * | 5/2008 | Mawhirt et al. ............. 356/39 |
| 2004/0073120 A1 | 4/2004 | Motz et al. |
| 2004/0090615 A1 * | 5/2004 | Dosmann et al. ............. 356/39 |
| 2005/0036147 A1 | 2/2005 | Sterling et al. |
| 2005/0250212 A1 * | 11/2005 | Azizian ............. 436/71 |

* cited by examiner

MODIFIED METHOD AND APPARATUS FOR MEASURING ANALYTES

FIELD OF INVENTION

The present application claims the benefit of U.S. Provisional Patent Application Ser. No. 60/738,526, filed Nov. 21, 2005, incorporated by reference herein.

FIELD OF INVENTION

The present invention relates to a method for measuring the concentration of a compound in a sample. The present invention also provides a device for carrying out the method.

BACKGROUND OF THE INVENTION

The concentration of a compound within blood of a subject may be measured using invasive techniques, for example obtaining a blood sample and placing the sample on a device that is introduced into a spectrophotometer. Alternatively, the concentration of the compound may be determined non-invasively by placing a part of the body within a receptor that is coupled to a spectrophotometer, as disclosed in for example, U.S. Pat. No. 5,361,758 (Hall et al.) or U.S. Pat No. 6,741,876 (Seciena et al.).

Clinical studies have revealed that the concentration of certain compounds in a body part of a subject may be used to assess the risk of development of specific medical conditions in that subject. Early detection of these types of risks in a patient permits measures to be taken that may slow or even prevent the onset of these conditions. As a non-limiting example, it has been determined that elevated concentration of cholesterol is an indication of a risk for coronary disease. Similarly, the determination of blood glucose levels is required by diabetic patients. Therefore, the development of simple, methods for determining the concentration of a compound is of importance.

In U.S. Pat. No. 6,365,363, Parfenov et al. describe a method of indirectly measuring the concentration of cholesterol in the skin of a subject by enzymatically oxidizing the cholesterol in a section of the subject's skin and then quantitating the amount of the hydrogen peroxide by product stoichiometrically formed in this reaction using a second enzymatic reaction. As a complex series of enzymatic reactions are used in this method to indirectly determine the concentration of cholesterol, the method is both costly and prone to error. In addition, the development of a result using this method is time consuming.

In U.S. Pat. Nos. 6,236,047 and 6,040,578, Malin et al. describe a method for determining the concentration of a blood compound using light in the near infrared range by analysing diffusively reflecting radiation emerging from the irradiated sample. Hall et al. also describe in U.S. Pat. No. 5,361,758 a non-invasive technique for directly measuring the concentration of constituents of blood using light in the near-infrared range.

Invasive methods for the assay of a compound involve lancing a body part to produce a blood sample and placing anywhere from about 2 to about 250 μl, or more, of the sample within a sample holding device are known, for example a slide well (U.S. Pat. No. 4,387,972, Valencia; U.S. Pat. No. 5,800,781. Gavin et al.; U.S. Pat. No. 5,207,984, Kheiri), a sample tab (e.g. WO 00/70350, Samsoondar) or filter paper strip or the like. The sample holder may then be introduced within a receptor of the sample holding device of a spectrophotometer to determine the concentration of the sample (e.g. WO 98/39634, Samsoondar; WO 99/47261, Samsoondar). This process may also require the use of additional devices, for example a capillary tube (e.g. U.S. Pat. No. 4,791,938, Valkenburg) to collect the sample from the body part and transfer the sample to the holding device.

SUMMARY OF THE INVENTION

The present invention relates to a method of measuring the concentration of a compound in a sample. The present invention also provides a device for carrying out the method.

It is an object of the invention to provide an improved method and apparatus for determining the concentration of a compound in a sample.

In a first aspect, the present invention provides a device for measuring one or more than one compound in a sample, comprising:

a source of electromagnetic radiation (EMR) that emits one or more than one wavelength of EMR, the source of EMR being operatively coupled to a power source;

a holder for receiving a detachable receptor, the holder comprising one or more than one input in operable association with the source of EMR, one or more than one output in operable association with a detector, the one or more than one input and the one or more than output of the holder in optical alignment with one or more than one port located within the receptor, the one or more than one input and the one or more than output defining an EMR path through the holder and within the receptor, wherein, the sample when received by the receptor is placed within the EMR path;

the detector for measuring transmitted or reflected EMR received from the sample, the detector operatively coupled to a processing system;

the processing system comprising one, or more than one calibration algorithm for determining a concentration for the one or more than one compound.

The detachable receptor of the device as described above may be sized to fit over a portion of a body part, sized to fit over a drop of blood located on the body part. Furthermore, the detachable receptor may comprise a matrix that can wick the sample off a surface of a body part. The detachable receptor, or the holder may further comprise an apparatus for lancing a body part when the body part is positioned with the receptor.

The device as described above may further comprise a second path of EMR though the holder and within the detachable receptor, wherein the second path of EMR interacts with the sample at a location separate from that of the EMR path, the second path of EMR is in operative association with the source of EMR or a second source of EMR.

The present invention also relates to the device described above wherein the sample is a body part and the device further comprises an alarm unit coupled to the processing system, the alarm unit producing an alarm signal when the concentration for the compound is outside or at a limit of a predetermined range of values of concentration for the compound.

The present invention also relates to the device described above wherein the sample is a body part and the device comprises an alarm unit coupled to the processing system, the alarm unit producing an alarm signal when the concentration for the compound is outside or at a limit of a predetermined range of values of concentration for the compound, and the receptor further comprises an apparatus for lancing the body part when the body part is within the receptor. The alarm signal serving as an indicator for the body part to be pierced within the receptor with the lancing apparatus to produce a sample of blood on the surface of the body part for analysis by the detector.

The present invention is also directed to the device as defined above, wherein the holder is a probe, and the probe may be removed from the source of EMR, the detector, or both the source of EMR and detector, but remain in optical association with the source of EMR and the detector.

The present invention also pertains to the device as defined above, wherein the source of EMR comprises wavelengths from about 300 nm to about 2500 nm, or from about 500 nm to about 1100 nm.

In a second aspect, the present invention provides a device for measuring one or more than one compound in a body part or a sample derived from a body part, comprising:

a source of electromagnetic radiation (EMR) that emits one or more than one wavelength of EMR, the source of EMR being operatively coupled to a power source;

a receptor comprising:

one or more than one input in operable association with the source of EMR, one or more than one output in operable association with a detector, the one or more than one input and the one or more than one output of the receptor in optical alignment with one or more than one port located within the receptor, the one or more than one input and the one or more than output defining an EMR path within the receptor, wherein, the body part or sample derived from a body part when received by the receptor is placed within the EMR path, and a piercing member for lancing the body part when the body part is positioned within the receptor to produce the sample derived from the body part;

the detector for measuring transmitted or reflected EMR received from the body part or from the sample, the detector operatively coupled to a processing system;

the processing system comprising one, or more than one calibration algorithm for determining a concentration for the compound, and a warning unit coupled to the processing system, the warning unit producing a signal when the concentration for the one or more than one compound is outside or at a limit of a predetermined range of values of concentration for the one or more than one compound.

Furthermore, the signal may also serving as an indicator for the body part to be pierced within the receptor with the lancing member to produce the sample derived from the body part for analysis.

The receptor of the device of the second aspect of the present invention, as described above, may be sized to fit over a portion of a body part, sized to fit over a drop of blood located on the body part. Furthermore, the receptor may comprise a matrix that can wick the sample off a surface of a body part. In another example, the receptor contains a protective sleeve for preventing contamination by the body part or a sample from the body part.

The device of the second aspect of the present invention, as described above, may further comprise a second path of EMR through the holder and within the receptor, wherein the second path of EMR interacts with the sample at a location separate from that of the EMR path, the second path of EMR is in operative association with the source of EMR or a second source of EMR.

The present application is also directed to the device of the second aspect of the present invention, as defined above, wherein the receptor is a probe, and the probe may be removed from the source of EMR, the detector, or both the source of EMR and detector, but remain in optical association with the source of EMR and the detector.

The present application also pertains to the device of the second aspect of the present invention, as defined above, wherein the source of EMR comprises wavelengths from about 300 nm to about 2500 nm, or from about 500 nm to about 1100 nm.

In a third aspect, the present invention provides a device for measuring one or more than one compound in a body part or a sample derived from a body part, comprising:

a source of electromagnetic radiation (EMR) that emits one or more than one wavelength of EMR, the source of EMR being operatively coupled to a power source;

a receptor comprising:

one or more than one input in operable association with the source of EMR, one or more than one output in operable association with a detector, the one or more than one input and the one or more than one output of the receptor in optical alignment with one or more than one port located within the receptor, the one or more than one input and the one or more than output defining an EMR path within the receptor, wherein, body part or sample derived from a body part when received within the receptor is placed within the EMR path, and an automated piercing mechanism for lancing the body part when the body part is positioned within the receptor to produce the sample derived from the body part, the piercing mechanism being coupled to a processing system for determining a concentration for the compound within the body part, the piercing mechanism being activated being activated upon receiving a signal from the processing system when the concentration for the compound in the body part is outside or at a limit of a predetermined range of values of concentration for the compound;

the detector for measurings transmitted or reflected EMR received from the body part or from the sample derived from the body part, the detector operatively coupled to the processing system, and the processing system comprising one, or more than one calibration algorithm for determining a concentration for the one or more than one compound in the body part or the sample derived from the body part.

The device of the third aspect of the present invention may further comprise an alarm or warning unit coupled to the processing system, the alarm unit producing an alarm signal when the concentration for the compound is outside or at a limit of a predetermined range of values of concentration for the compound, the alarm signal also serving as an indicator that the body part will be pierced by the piercing mechanism when the body part is positioned within the receptor.

The receptor of the device of the third aspect of the present invention, as described above, may be sized to fit over a portion of a body part, sized to fit over a drop of blood located on the body part. Furthermore, the receptor may comprise a matrix that can wick the sample off a surface of a body part. In another example, the receptor contains a protective sleeve for preventing contamination by the body part or a sample from the body part.

The device of the third aspect of the present invention, as described above, may further comprise a second path of EMR through the holder and within the receptor, wherein the second path of EMR interacts with the sample at a location separate from that of the EMR path, the second path of EMR is in operative association with the source of EMR or a second source of EMR.

The present application is also directed to the device of the third aspect of the present invention, as defined above, wherein the receptor is a probe and the probe may be removed from the source of EMR, the detector, or both the source of EMR and detector, but remain in optical association with the source of EMR and the detector.

The present application also pertains to the device of the third aspect of the present invention, as defined above, wherein the source of EMR comprises wavelengths from about 300 nm to about 2500 nm, or from about 500 nm to about 1100 nm.

In a fourth aspect, the present invention provides a method (A) of determining the concentration of a compound in a sample of blood comprising, (a) placing a receptor over a portion of a body part, the body part having a sample of blood thereon, (b) directing a source of electromagnetic radiation (EMR) through the receptor and onto the sample of blood;

(c) measuring a quantity of the EMR reflected by, or transmitted through, the sample of blood with a detector; and (d) performing a quantitative mathematical analysis of the quantity of EMR using an algorithm, and determining the concentration of the compound in the sample of blood.

The present invention pertains to the method (A) as defined above, wherein the compound may be selected from the group consisting of a fat, a protein, a glycoprotein, hemoglobin, Oxy-Hb, % oxy-Hb, "Oxy-Hb plus Deoxy-Hb". "Total-Hb minus Met-Hb", Met-Hb, % met-Hb, Carboxy-Hb, Co-Hb, Sulf-Hb, cholesterol, glucose, plasma glucose, interstitial glucose, % plasma glucose, % interstitial glucose, a fat, a protein, a glycoprotein, a lipoprotein, a carbohydrate, a steroid, an amino acid, nitrogen, carbon dioxide, cortisol, creatine, creatinine, a ketone, a lipid, urea, a fatty acid, glycosolated hemoglobin, alcohol, lactate, an ion, $Ca^{2+}$, $K^+$, $Cl^-$, $HCO_3^-$ and $HPO_4^-$.

The present invention embraces the method (A) as described above, wherein prior to the step of placing (step a)), the body part is lanced so that the sample of blood is produced on the surface of the body part. Prior to the step of placing (step (a)), the receptor is placed within a holder, and after the step of measuring (step (c)) the receptor is removed from the holder. Furthermore, the present invention includes the method (A) as defined above, wherein in the step of placing (step (a)), the sample may be wicked within the receptor. The present invention also provides for the method (A) as defined above, wherein the source of EMR comprises wavelengths from about 300 nm to about 2500 nm, or from about 500 nm to about 1100 nm.

The present invention also pertains to the method (A) as defined above, wherein in the step of directing (step (b)), a second source of EMR is directed to the body part, and a measurement of background is obtained. Alternatively, the second source of EMR may be directed to the body part, and in the step of measuring (step (c)), a non-invasive measurement is made of one or more compound within the body part.

In a fifth aspect, the present invention provides The present invention also pertains to a method (B) of determining the concentration of a compound in a sample of blood comprising, (a) placing a receptor over a portion of a body part;

(b) lancing the body part located within the receptor to produce a sample of blood on the surface of the body part, (c) directing a source of electromagnetic radiation (EMR) through the receptor and onto the sample of blood;

(d) measuring a quantity of the EMR reflected by, or transmitted through, the sample of blood with a detector; and (e) performing a quantitative mathematical analysis of the quantity of EMR using an algorithm, and determining the concentration of the compound in the sample of blood.

The present invention pertains to the method (B) as defined above, wherein the compound may be selected from the group consisting of a fat, a protein, a glycoprotein, hemoglobin, Oxy-Hb, % oxy-Hb, "Oxy-Hb plus Deoxy-Hb", "Total-Hb minus Met-Hb", Met-Hb, % met-Hb, Carboxy-H-b, Co-Hb, Sulf-Hb, cholesterol, glucose, plasma glucose, interstitial glucose, % plasma glucose, % interstitial glucose, plasma glucose, interstitial glucose, % plasma glucose, % interstitial glucose, a fat, a protein, a glycoprotein, a lipoprotein, a carbohydrate, a steroid, an amino acid, nitrogen, carbon dioxide, cortisol, creatine, creatinine a ketone, a lipid, urea, a fatty acid, glycosolated hemoglobin, alcohol, lactate, an ion, $Ca^{2+}$, $K^+$, $Cl^-$, $HCO_3^-$ and $HPO_4^-$.

The present invention is directed to the method (B) as defined above, wherein prior to the step of placing (step (a)), the receptor is placed within a holder, and after the step of measuring (step (c)) the receptor is removed from the holder. Furthermore, in the step of placing (step (a)), the sample may be wicked within the receptor.

The present invention also provides for the method (B) as defined above, wherein the source of EMR comprises wavelengths from about 300 nm to about 2500 nm, or from about 500 nm to about 1100 nm.

Using the device and method of the present invention, the measured concentration of the one or more than one compound may also be correlated to a specific clinical condition or to the propensity for a specific clinical condition.

In a sixth aspect, the present invention provides a method (C) of determining the concentration of a compound in blood within a body part:

(a) determining when the concentration for the compound measured using a non-invasive method is outside or at a limit of a predetermined range of values of concentration;

(b) placing a receptor over a portion of a body part, the body part having a sample of blood thereon, (c) directing a source of electromagnetic radiation (EMR) through the receptor and onto the sample of blood:

(d) measuring a quantity of the EMR reflected by, or transmitted through, the sample of blood with a detector; and (e) performing a quantitative mathematical analysis of the quantity of EMR using an algorithm, and determining the concentration of the compound in the sample of blood.

The present application also relates to the above-defined method (C), wherein the step of determining (step (a)) comprises detecting an alarm signal produced by a non-invasive device used to measure the concentration of the compound in the non-invasive method.

The present application also relates to the above-defined method (C) of the present invention, wherein the non-invasive method comprises:

placing the receptor over a portion of a body part;

directing a source of electromagnetic radiation (EMR) through the receptor and onto the body part;

measuring a quantity of the EMR reflected by, or transmitted through the body part with a detector; and performing a quantitative mathematical analysis of the quantity of EMR using, an algorithm, and determining the concentration of the compound.

The present invention pertains to the method (C) as defined above, wherein the compound may be selected from the group consisting of a fat, a protein, a glycoprotein, hemoglobin, Oxy-Hb, % oxy-Hb, "Oxy-Hb plus Deoxy-Hb". "Total-Hb minus Met-Hb", Met-Hb, % met-Hb, Carboxy-Hb, Co-Hb. Sulf-Hb, cholesterol, glucose, plasma glucose, interstitial glucose, % plasma glucose, % interstitial glucose, a fat, a protein, a glycoprotein, a lipoprotein, a carbohydrate, a steroid, an amino acid, nitrogen, carbon dioxide, cortisol, creatine, creatinine, a ketone, a lipid, urea, a fatty acid, glycosolated hemoglobin, alcohol, lactate, an ion, $Ca^{2+}$, $K^+$, $Cl^-$, $HCO_3^-$ and $HPO_4^-$.

The present invention embraces the method (C) as described above, wherein prior to the step of placing (step a)), the body part is lanced so that the sample of blood is produced on the surface of the body part. Prior to the step of placing (step (a)), the receptor is placed within a holder, and after the step of measuring (step (c)) the receptor is removed from the holder. Furthermore, the present invention includes the method (A) as defined above, wherein in the step of placing (step (a)), the sample may be wicked within the receptor. The present invention also provides for the method (A) as defined above, wherein the source of EMR comprises wavelengths from about 300 nm to about 2500 nm, or from about 500 nm to about 1100 nm.

By determining the concentration of a compound within a sample localized on a surface of a body part, minimal volumes of the sample, for example blood, are required. Furthermore, by placing the receptor of the device directly over the sample, a minimal amount of sample handling is required prior to assay. Providing a receptor that combines the lancing of the body part within the receptor, ensures alignment of the sample within the receptor with the source of EMR, so that the path of EMR interacts with the sample with minimal background effects. Similarly, by providing a receptor that wicks the sample from the surface of the body part and towards the input and output ports of the receptor, ensures that the sample is in optical alignment with the path of EMR and retained within the receptor. The device and methods for obtaining a concentration of a compound within the sample as disclosed herein result in a safe, simple, and efficient method of assaying a compound within a sample. Furthermore, since there is no sample handling, the method and device of the present invention requires the use of a minimal amount of sample for the determination procedure.

The present invention also provides a device for measuring one or more than one compound in a sample, comprising:

a source of electromagnetic radiation (EMR) that emits one or more than one wavelength of EMR, the source of EMR being operatively coupled to a power source;

one or more than one receptor for receiving a body part (non-invasive) and a sample holder (invasive) as the sample, the one or more than one receptor optically coupled to the source of EMR by one or more than one radiation guiding element, the radiation guiding element comprising one or more than one input in operable association with the source of EMR, one or more than one output in operable association with a detector, part the one or more than one input and the one or more than output in optical alignment with one or more than one port located within the one or more than one receptor, the one or more than one input and the one or more than one output defining an EMR path from the source, through the one or more than one receptor and the detector, wherein, the sample when received by the one or more than one receptor is placed within the EMR path;

the detector for measuring transmitted or reflected EMR received from the sample, the detector operatively coupled to a processing system;

the processing system comprising one, or more than one calibration algorithm for determining a concentration for the one or more than one compound.

Furthermore, the one or more than on receptor may comprise a first receptor for receiving a body part, and a second receptor for receiving a sample holder. Alternatively, the one or more than on receptor may comprise one receptor, the one receptor for receiving a body part, and an insert, the insert for receiving a sample holder. The device may also comprising a warning unit coupled to the processing system, the warning unit producing a signal when the concentration for the compound is outside or at a limit of a predetermined range of values of concentration for the compound.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
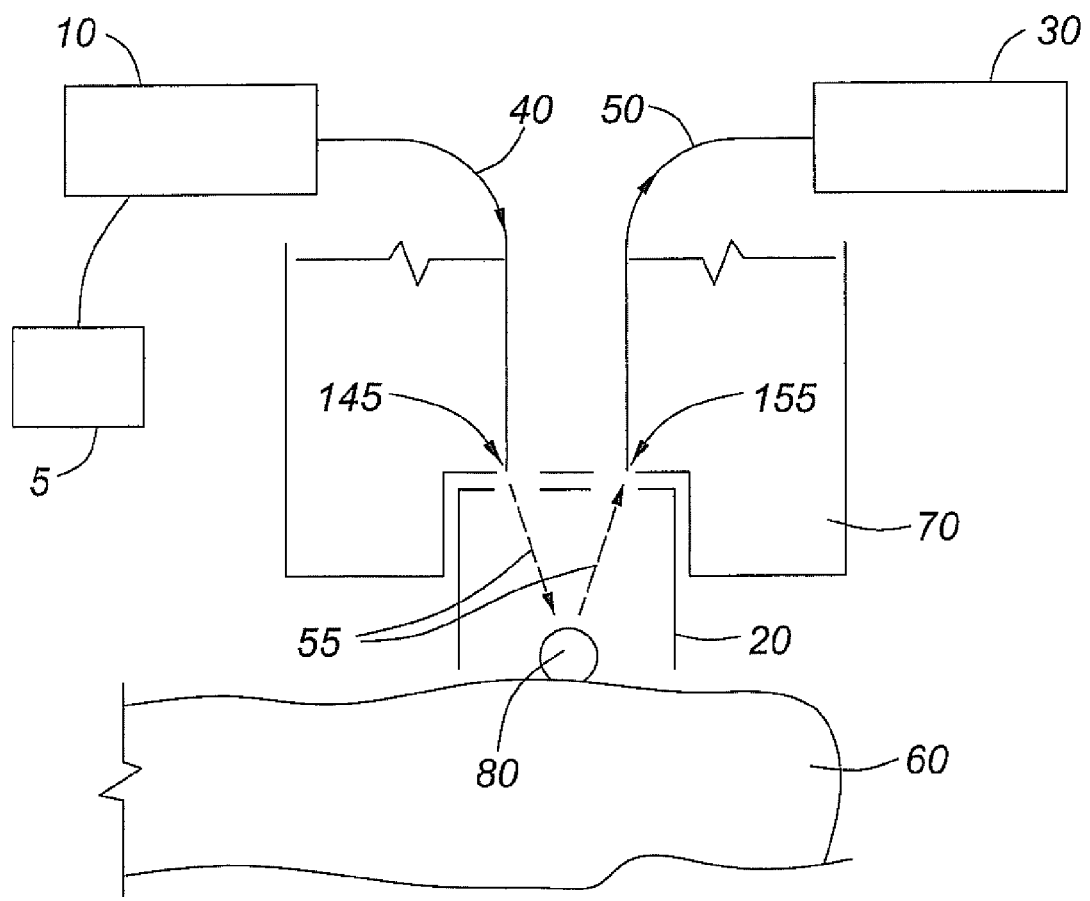
FIG. 1 shows a device (1) in accordance with an embodiment of the present invention placed over a body part (60) with a sample (80) located on the surface pf the body part and within a receptor (20).

The present invention relates to a method of measuring the concentration of a compound in a sample. The present invention also provides a device for carrying out the method.

The following description is of a preferred embodiment.

With reference to FIGS. 1-6, there is shown an aspect of an embodiment of the present invention. Alternate embodiments are shown in FIGS. 7-10. In FIGS. 1-6 there is shown a device (1) for measuring a concentration of one or more than one compound in a sample. The device comprises a source of electromagnetic radiation (EMR; 10), a holder (70) for receiving a receptor, the receptor (20), and a detector (30), wherein the source of EMR, the holder, the receptor and the detector are in an operative optical association, so that a path of EMR from the source of EMR, through the holder and receptor to the detector may be established. When a sample (80) is placed within the receptor (20), a parameter of one or more compounds within the sample may be determined and the result displayed on a screen (165, see FIG. 4).

The source of EMR (10) preferably emits one or more than one wavelength of EMR. For example, which is not to be considered limiting in any manner, the source of EMR may emit one or more than one wavelength of EMR over a range of wavelengths from about 300 nm to about 20,000 nm, or any wavelength therebetween as desired. For example from about 300 nm to about 3,000 nm or any wavelength therebetween, or from about 500 nm to about 2,500 nm or any wavelength therebetween. The source of EMR may be a polychromatic source, an LED source, a laser source, or another source suitable for irradiating a sample at one or more than one desired wavelengths. The source of EMR, and the range of wavelengths emitted by the EMR source is not to be considered limiting in the present invention. The source of EMR is operatively coupled to any suitable power source (5) as would be known to one of skill in the art.

The near infrared region of the electromagnetic spectrum is generally considered to be the spectral interval extending from 650 nm through to 2700 nm and measurements of samples as described herein may be obtained from about 700 nm to about 1100 nm range. Absorption bands observed in this interval are primarily the combination and overtone bands of the fundamental infrared bands. Although very weak in intensity, being typically less than one-tenth in intensity of the fundamental infrared bands, these bands are considered to be analytically useful because nearly all chemical species exhibit characteristic absorption bands in this spectral interval. The near infrared region is particularly well-suited to invasive and non-invasive diagnostic applications because biological samples, or human tissue are somewhat transparent to the incident radiation and therefore sufficient penetration of the radiation is possible to allow accurate quantitative analysis.

The source of EMR used in the present invention to detect the one or more than one compound in the sample or body part is preferably near-infrared light, for example but not limited to a polychromatic light source. This type of light source can emit light over a very wide bandwidth including light in the near infrared spectrum. In this case, the light from the light source preferably passes first through a collimator, which is a collection of lenses that concentrate the light into a narrow parallel beam directed at the receptor. The polychromatic light source can comprise a quartz-halogen or a tungsten-halogen bulb to provide the broad spectrum of light in the near infrared, and is powered by a stabilized power source, for example, a DC power supply, or by a battery. This polychromatic light source may be a tungsten-halogen lamp or it may be a collection of LEDs or other light sources selected to emit radiation in the range of about 650 to about 1100 nm. More particularly, the polychromatic is light source comprises a source of light that emits a wavelength of light in the visible red spectrum, for example, 660 nm, a wavelength of light in the infrered spectrum, for example, 940 nm, and a broad spectrum of light in the near infrared region.

In a particular non-limiting example, the polychromatic light source may comprise a pair of light emitting diodes that provide light at the wavelengths of 660 nm and 940 nm for detecting the value of oxygen saturation of blood in the part, and a broadband light source that emits a broad spectrum of light in the near infrared. Additional sources of EMR may also be used to determine the concentration of additional compounds with the sample. The light emitting diodes and the broadband light sources may be activated simultaneously, or sequentially so that the concentration of the compound in the sample or body part, and the value of oxygen saturation in the blood are either determined simultaneously, or in a stepwise manner. In another non-limiting example, spectra of a sample may be obtained and different regions, or one or more than one specific wavelength may be compared to determine relative amounts, concentrations, or % compositions of one or more than one compound, for example but not limited to the % amount of a compound within the plasma (as a function of total compound, or of the plasma plus interstitial compound levels), or % compound within interstitial fluid (as a function of total, or of the plasma plus interstitial compound levels), for example % plasma glucose, or % interstitial glucose. The one or more than one compound, the oxygen saturation, % plasma glucose, % interstitial glucose, or a combination thereof, may be determined as a concentration value, or as a percentage, for example, a percentage of one compound relative to one or more than one other compound in the sample. In addition, the light emitting diodes may be cycled on and off, many times per second, during the process of acquiring absorbance or transmission data to help eliminate background noise.

In one embodiment of the present invention, the device (1) may be fitted with a holder (70) for receiving a detachable receptor (20), as shown if FIG. 1. The holder comprises one or more than one radiation guiding elements, for example one or more than one input (40) in operable association with the source of EMR (10), and one or more than one output (50) in operable association with the detector (30). The one or more than one input (40) and the one or more than output (50) of the holder (70) are in an optical alignment with one or more than one port located within the holder (see 145, 155, FIG. 1) and one or more than one port within the receptor (see 140, 150, FIG. 2). The one or more than one input (40) and the one or more than output (50) defining a path of EMR through the holder and within the receptor (e.g. 55), when, the sample (80) is received by the receptor (20) and placed in the path of EMR (55). In the example shown in FIGS. 1 and 2, two ports are shown within the holder and receptor (140, 145, and 150, 155). However one port may be used (157, FIG. 3), or more than one or two ports may be used, if additional EMR paths are to be used.

Figure 7:
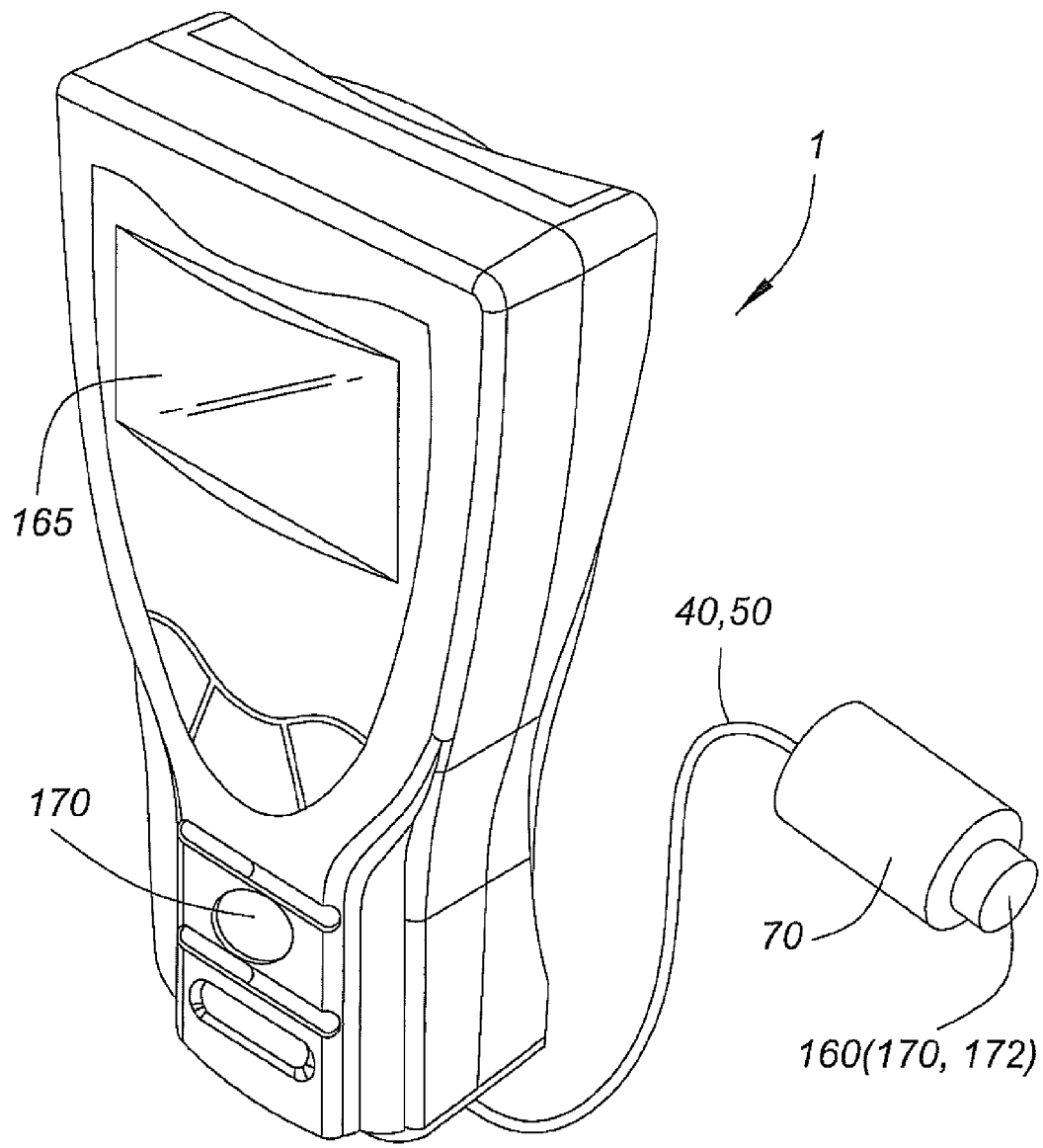
FIG. 7 shows a hand held device with a detachable probe in accordance with a further embodiment of the present invention.

In an alternate embodiment of the present invention the receptor may be an integral part of apparatus (1), for example as shown as 160 (FIG. 4), or 170 (FIG. 7). Receptor, 160 (FIG. 4) is of a shape and configuration to receive a sample holder containing an in vitro sample, for example but not limited to, a sample tab (WO 00/70350, which is incorporated herein by reference), a slide well (U.S. Pat. No. 4,387,972, Valencia; U.S. Pat. No. 5,800,781, Gavin et al.; U.S. Pat. No. 5,207,984. Kheiri; which are incorporated herein by reference), a filter paper strip or the like, or a capillary tube (e.g. U.S. Pat. No. 4,791,938 which is incorporated herein by reference). The capillary tube may be collect the sample from the body part and either be directly inserted within the receptor, or the sample within the capillary tube may be transferred to the sample to a holding device. The sample holder may then be introduced within receptor of the sample holding device 160 of device (1), to determine the concentration of the sample. Receptor 170 is of a size and shape to received a body part, for example but not limited to a finger.

Figure 8:
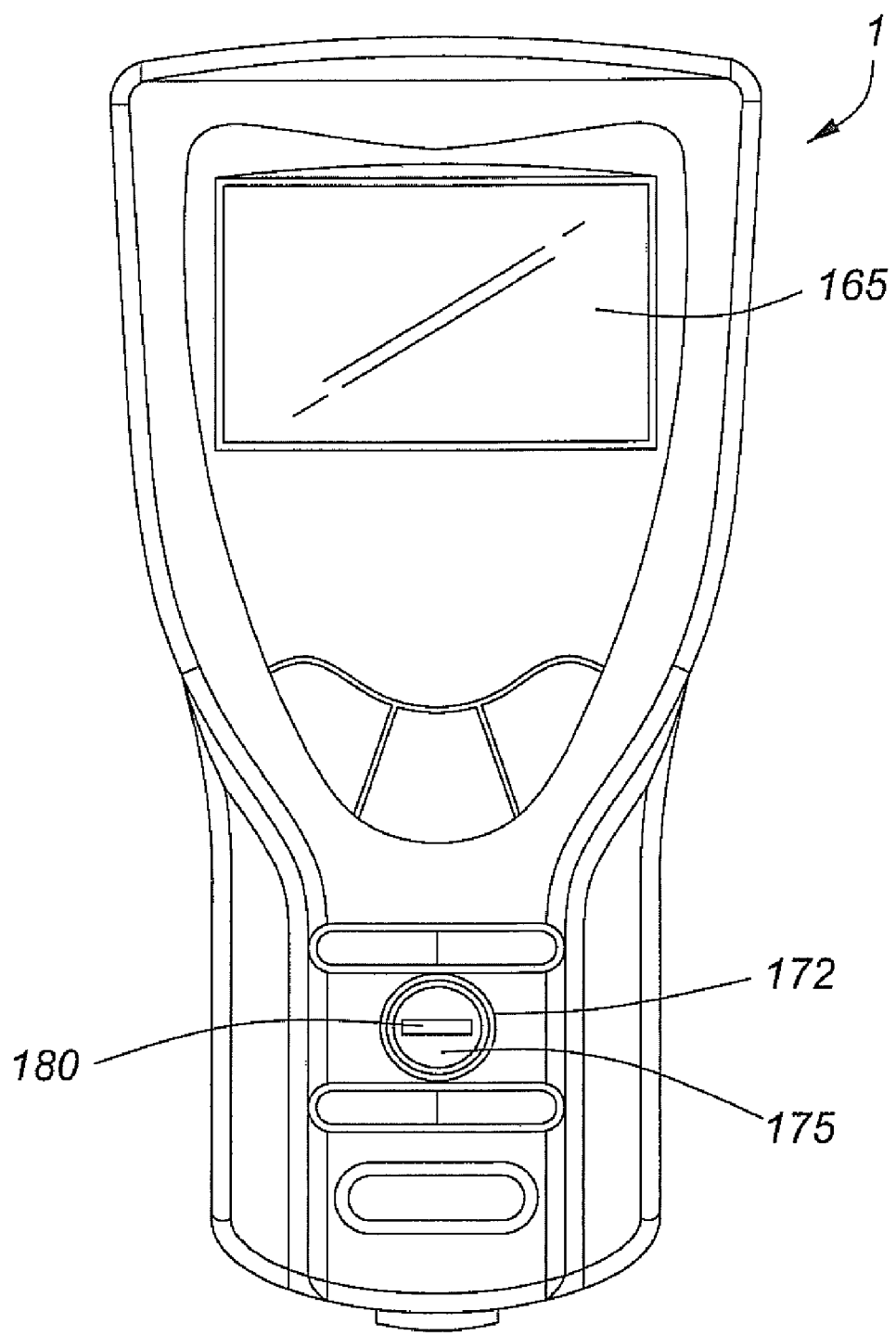
FIG. 8 shows a perspective view of an alternate hand held device of the present invention.
Figure 9:
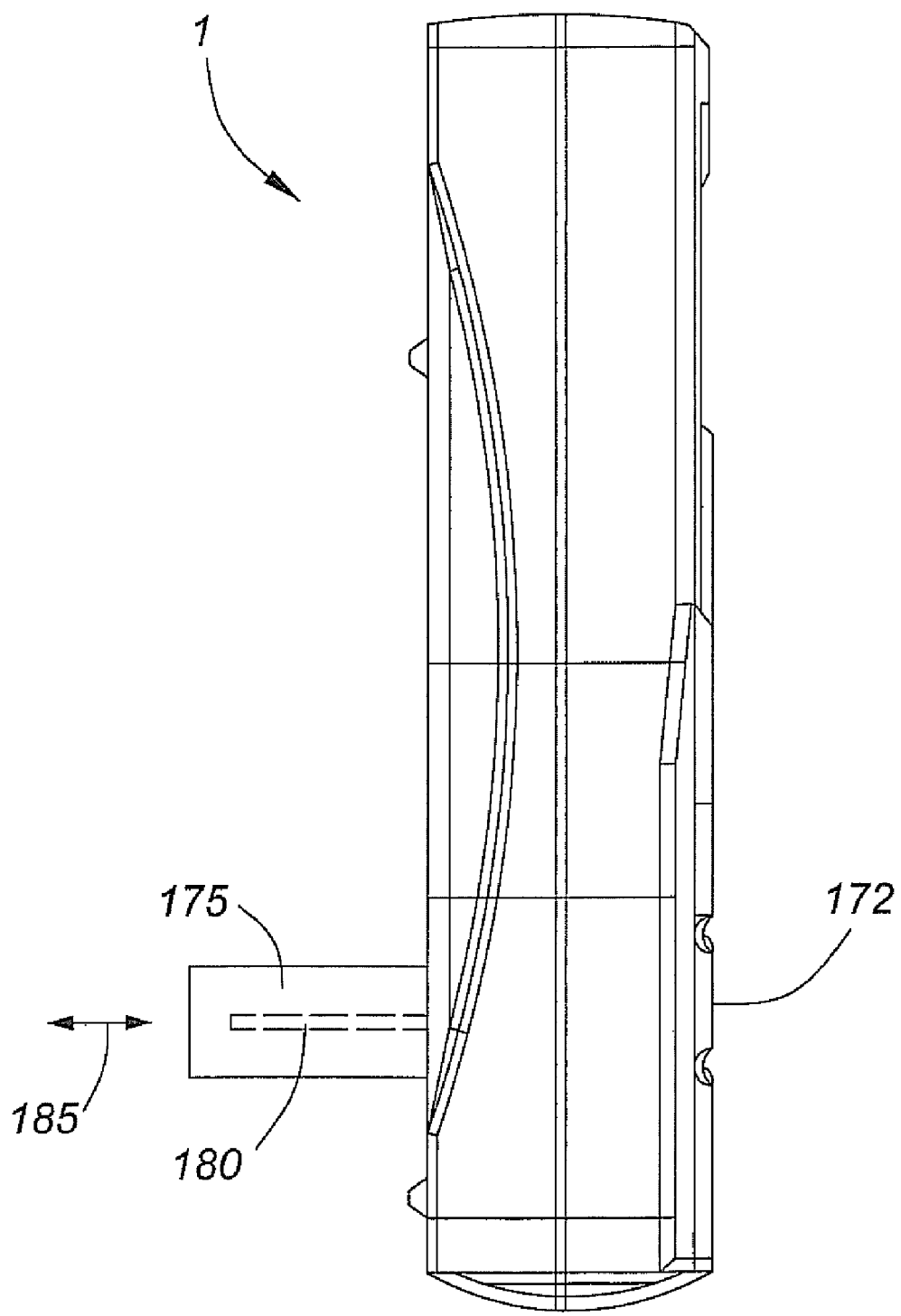
FIG. 9 shows a side view of the hand held device of FIG. 8.
Figure 10:
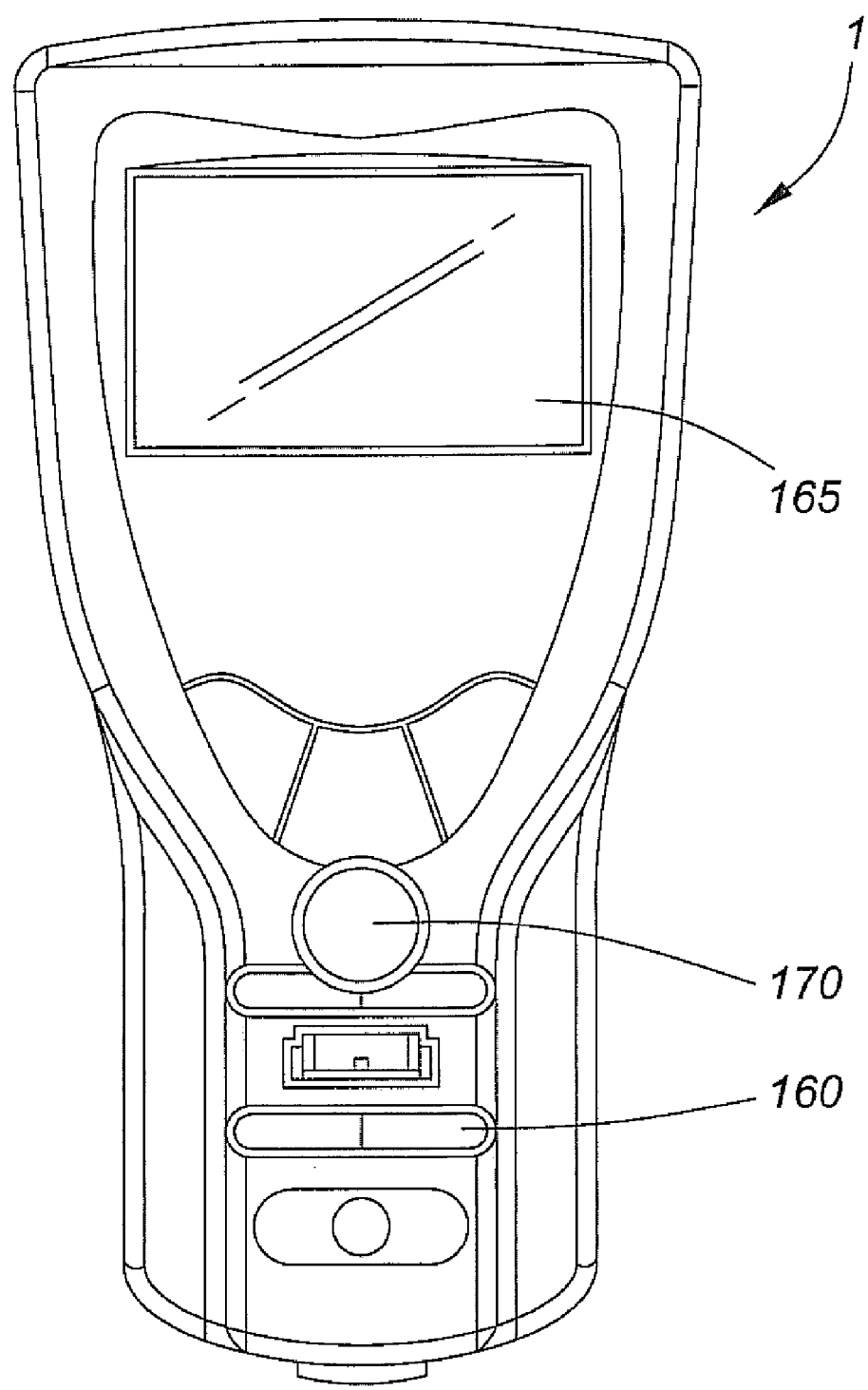
FIG. 10 shows a front view of an alternate hand held device of the present invention.

Receptor 160 and 170 may be combined within the device (1) as shown in FIGS. 8 and 9, as a multi-receptor (172) where the multi-receptor is of a size and shape to receive both a body part or a sample holder, or the device may comprise separate receptors (160 and 170) as shown in FIG. 10 that receive either a sample holder (160) or a body part (170). Alternatively, the device (1) may comprise one receptor, either 160 or 170, and a probe comprising a separate holder (70, FIGS. 5, 7) in optical communication (via 40, 50) with the device. The separate holder comprises the alternate receptor, either 170 or 160, from that within the device. In the non-limiting example shown in FIG. 5, the device (1) comprises the receptor for the sample holder (160), and the separate holder (70) comprises the receptor for the body part (170). In FIG. 7, an alternate arrangement is shown, where the device comprises receptor 170 for a body part, and the separate holder (70) comprises receptor 160 for the sample holder. The probe may be attached to the device (1) via radiation guiding elements, for example an optical cable comprising input (40) and output (50), in a permanent manner, or it may plug into the device as required via a receptacle within the device.

A device comprising both receptors (160, 170, 172), or a device comprising a receptor and a probe comprising a receptor and in optical communication with the device, may be used for the determination of one or more compounds in a variety of samples. For example, if the sample is a body part, then the one or more than one compound within the sample is determined non-invasively, (i.e. an in vivo sample) using receptor 170 (FIGS. 5, 8 and 9) or 172 (FIG. 10). If the sample is within a sample holder, then the one or more than one compound within the sample is determined using invasive techniques (i.e. an in vitro sample). In the devices shown in FIGS. 8-10, both sample types may be received by the receptor or receptors and the one or more than one compound determined within the sample.

In the embodiment shown in FIGS. 8 and 9, receptor 172 comprises an opening of a size and shape to receive a body part, for example but not limited to a finger that may be inserted within receptor 172, and an insert (175) that is designed to accept a sample holder within the sample holder receptor (180). In this example, the insert (175) may be removed to permit insertion of the body part into the receptor (172). The insert (175) may be pulled out, or the insert may be displaced as a result of the body part being placed within the receptor (172), for example as shown in FIG. 10. Following a determination of the one or more than one compound within the body part using receptor 172, the insert (175) may then be reinserted within receptor 172, either manually (if it is removed from the receptor), pushed back in place, if it is displaced by the body part, or re-inserted via a biasing device such as a spring, and the sample holder placed within the sample holder receptor (180) and a second determination of one or more than one compound obtained. A displaceable receptor (172) may also be used within a probe (70, FIG. 5 and 7).

As described in more detail below, the device (1) may comprise an alarm, signal system, or display (e.g. on screen 165), so that if following an in vitro sample determination using a body part placed within receptor (170), the level of the one or more than one compound is outside a preset range, then the alarm signal or display, is activated. The alarm, signal or display may, in one example notify the user to remove the body part from the device, obtain an in vitro sample, place the in vitro sample into the sample holder, and insert the sample holder within receptor (160) of the device to obtain an in vitro determination of the one or more than one compound. Alternatively, the alarm, signal or display may activate an automated lance and obtain an invasive sample for analysis. In this way device (1) can be used for an accurate determination of the one or more than one compound using a combination of both in vivo (non-invasive) and in vitro (invasive) techniques.

The radiation guiding elements (40, 50, FIGS. 1, 2, 3, 5 and 7) may be any suitable element for transmitting radiation, for example but not limited to one or more than one fiber optic bundles, or radiation guiding rods, for example but not limited to fused silica rods. The radiation guiding elements may also be coupled together, so that for example the input path of EMR may pass through an optical fiber oriented circumferentially around a central optical fiber that is used to receive the output EMR, or visa versa. Additional beam-forming elements such as lenses (e.g. 90, 100, FIG. 2) or mirrors may be fitted in the holder and used if desired to ensure that the path of EMR (55) is directed to the sample (80) within the receptor. However, the optical fibers may also be positioned, in the absence of lenses or other path-focusing or directing elements, in a manner that ensures that the path of EMR (55) is directed to the sample (80) within the receptor. If a coupled optical fiber is used (i.e. a fiber carrying both input and output EMR), then one port (157, FIG. 3), or one port and a lens (105), may be used within the holder (70) to input and receive the EMR. The holder (20) or receptor (160, 170) may be located within the spectrophotometric device, for example, a hand held device (160, FIGS. 4 and 10; 170, FIGS. 7 and 10; or 172, FIGS. 8 and 9), or located within a holder or probe (70, FIGS. 5 and 7) that is in optical association with the spectrophotometer housing the source of EMR (10) and the detector (30), through optical fibers (40, 50) and the like (see FIG. 5). In this manner, the holder may be in operative association with, and detachable from, the source of EMR, the detector, or both the source of EMR and detector, and may be used, for example, for use with larger spectrophotometric devices.

The receptor (20, 160, 170, 172) may comprise one or more than one input and one or more than one output ports (e.g. 157, FIG. 3, 140, 150, FIG. 2) that are in optical alignment with the input and outputs of the holder (e.g. 105, FIG. 3, 145, 155, FIG. 1) to permit entry of EMR (55) from the holder (70) to the receptor (20, 160, 170, 172), and its return to the holder following interaction of the EMR with the sample (80).

In a device that comprises two receptors (160 and 170, FIGS. 5, 7 and 10) or a dual receptor (172, FIGS. 8, 9) that accepts both a sample that is a body part (receptor, 170) and a sample holder (receptor 175), the source of EMR may be split to the input (40) and output (50) radiation guiding elements so that each receptor receives EMR as required. The light path to (40) and from (50) each receptor may be shuttered so that stray light does not enter the system. For example, the shutter may close or interrupt the light path when the receptor is empty, while placing a sample within the receptor may open the shutter to permit the light path to interact with the sample and the detector (30). Alternatively, the device may comprise two sets of radiation guiding elements each having and input (40) and an output (50). In this embodiment, a splitter may be used to divert the EMR from the source (10) to one set of radiation guiding elements comprising both an input (40) and an output (50) that is directed to and from receptor (160) for the determination of an in vitro (invasive) sample within a sample holder. If an in vitro or non-invasive sample is to be obtained, then the splitter may be used to divert the EMR from source (10) to a second set of radiations guiding elements directing and receiving the EMR from receptor (170). If the multi-receptor (172) is used, then the first and second set of radiation guiding elements may be the same. However, in each of the cases outlined above, different spectral qualities of the EMR may be desired for each sample-type placed with the respective receptors. For example, different regions of a range of wavelengths or specific wavelengths may be selected, depending on the sample or the one or more than one compound being determined. If the spectral quality of the EMR is to be altered to conform with the sample or compound being assayed, then a signal may be sent to the source of EMR (10) to select the appropriate wavelength or range of wavelengths required for the sample. The signal may be activated when a receptor is being used, or the spectral quality of the EMR may be selected manually though a switch, button, or via the screen (165). The spectral quality of the EMR may also be selected automatically after the signal, alarm or display is activated as a result of an in vivo (non-invasive) reading being obtained that is outside of a target spectral range and the following reading to be determine is with an invasive sample 9 using a sample holder).

In the embodiment where the receptor (20) matingly engages with the holder (70), the receptor can easily be removed from the holder after use. The receptor may be in press fit engagement with the holder, snap into place, be retained via any suitable biasing means, for example a spring, and the like. If desired, a tab may be added to the receptor to facilitate installation and removal of the receptor from the holder.

The receptor (20) may be sized to fit over the sample (80) located on the surface of a body part (60) as shown in FIG. 1, or it may be sized to receive the body part (60), and sample (80) as shown in FIGS. 2 and 6-10. Preferably, the placement of the receptor over the body part ensures removal of a substantial amount of stray ambient light during the measurement. If the receptor fits over the body part as shown in FIGS. 2 and 6-10, then a light shield (110, FIG. 2) may be used that fits around the body part when it is placed in the receptor.

Figure 6:
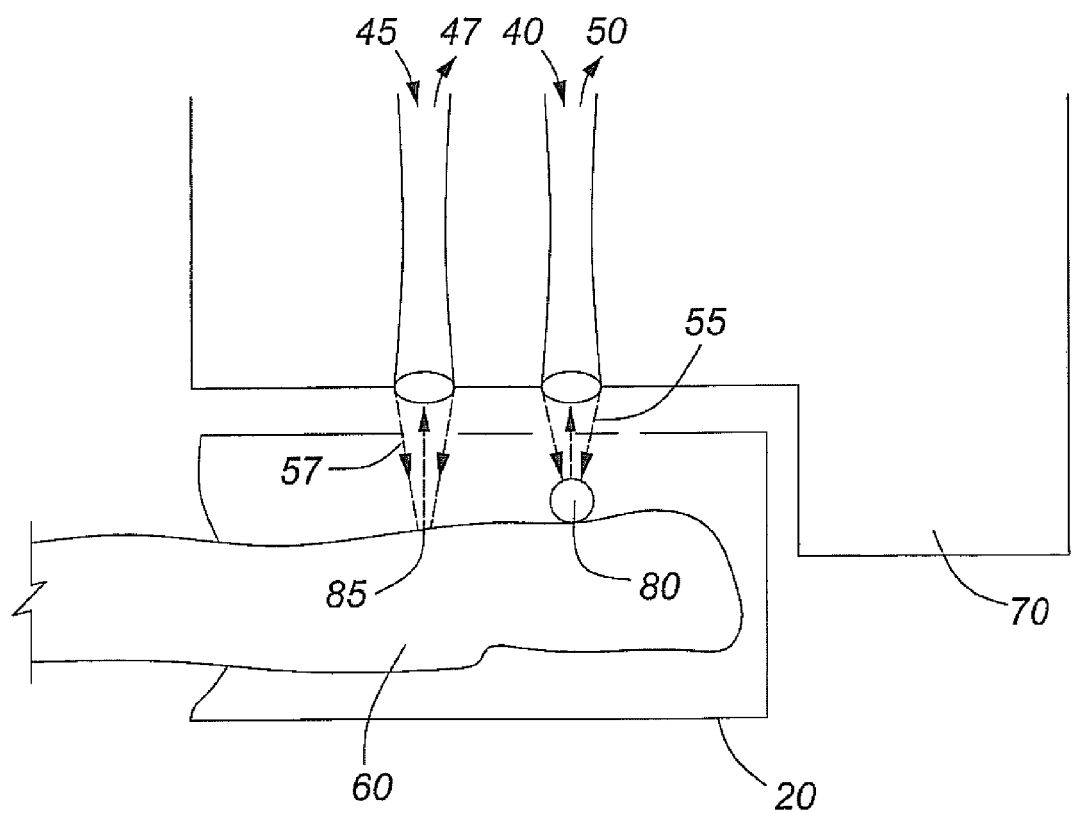
FIG. 6 shows a receptor (20) and holder (70) in accordance with a further embodiment of the present invention.

If the receptor is to be exposed to blood during use, then the receptor may be made from a material that can be discarded after use to minimize contamination from the sample. Alternatively, a non-discarded receptor may be used if the receptor is located within device (1) or holder (70), as shown in FIGS. 7-10. In this latter case, it is preferred that the receptor is used for in vivo (non-invasive) measurements. However, if the receptor is integral with the device, and invasive measurements are obtained (e.g. as shown in FIGS. 2 and 6), then a sleeve or insert may be used to reduce contamination of the inside surfaces of the receptor.

The receptor may also comprise a material (25, FIG. 3) that wicks the sample away from the skin surface, towards the input and output ports of the receptor, and into the path of the EMR within the receptor. For example, which is not to be considered limiting in ay any manner, the sample may be immobilized within the receptor by absorption or capillary action, within filter paper, glass wool, one or more than one capillary tubes made from polymeric or other rigid or semi rigid material, or any other material known to wick a liquid sample. Preferably, the material used is transparent to the wavelength of light used in the device. The immobilized sample within the receptor is then irradiated with EMR in order to assay one or more than one compound with the sample. With this arrangement, the sample is immobilized and retained within the receptor. By removing the sample from the body part, this also ensures minimal contamination from the sample, during use. After the sample is immobilized within the receptor, a measurement of one or more that one compound may be obtained as described above, or the device, or probe holding the receptor may be removed from the body part and the measurement obtained. If required, an opaque cover may be fitted over the receptor to block ambient light during the measurement of the sample. After the measurement is taken, the receptor may then be removed and discarded from the holder of the device or probe.

Figure 2:
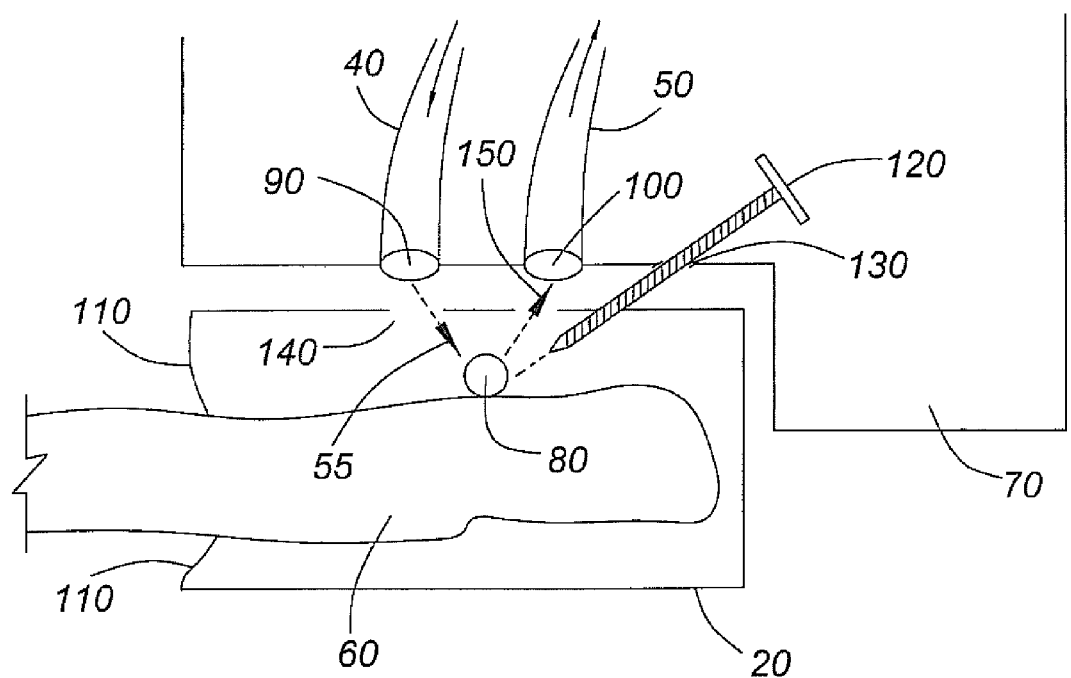
FIG. 2 shows a receptor (20) and holder (70) in accordance with a further embodiment of the present invention.
Figure 3:
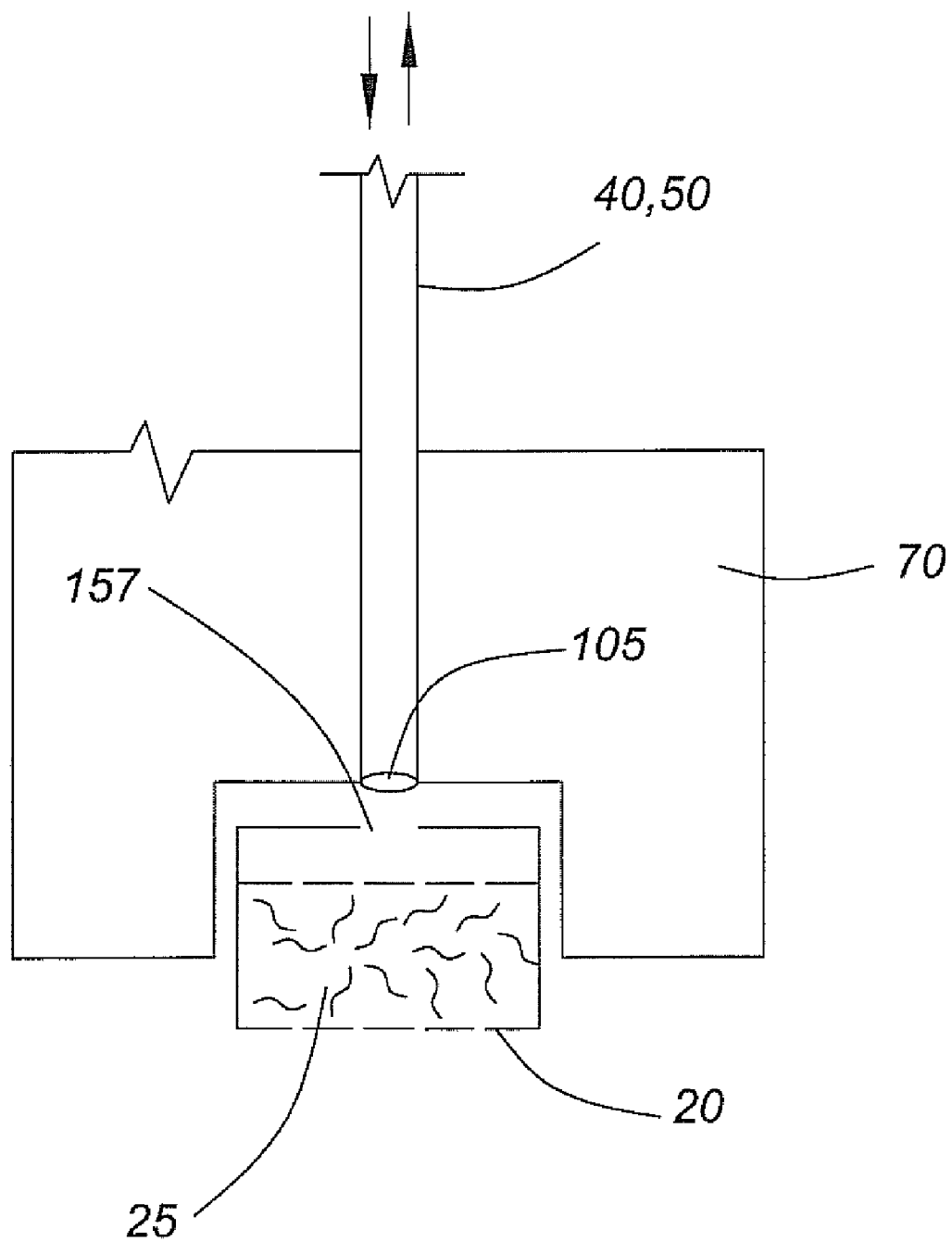
FIG. 3 shows a receptor (20) and holder (70) in accordance with a further embodiment of the present invention comprising a wicking material (25).
Figure 4:
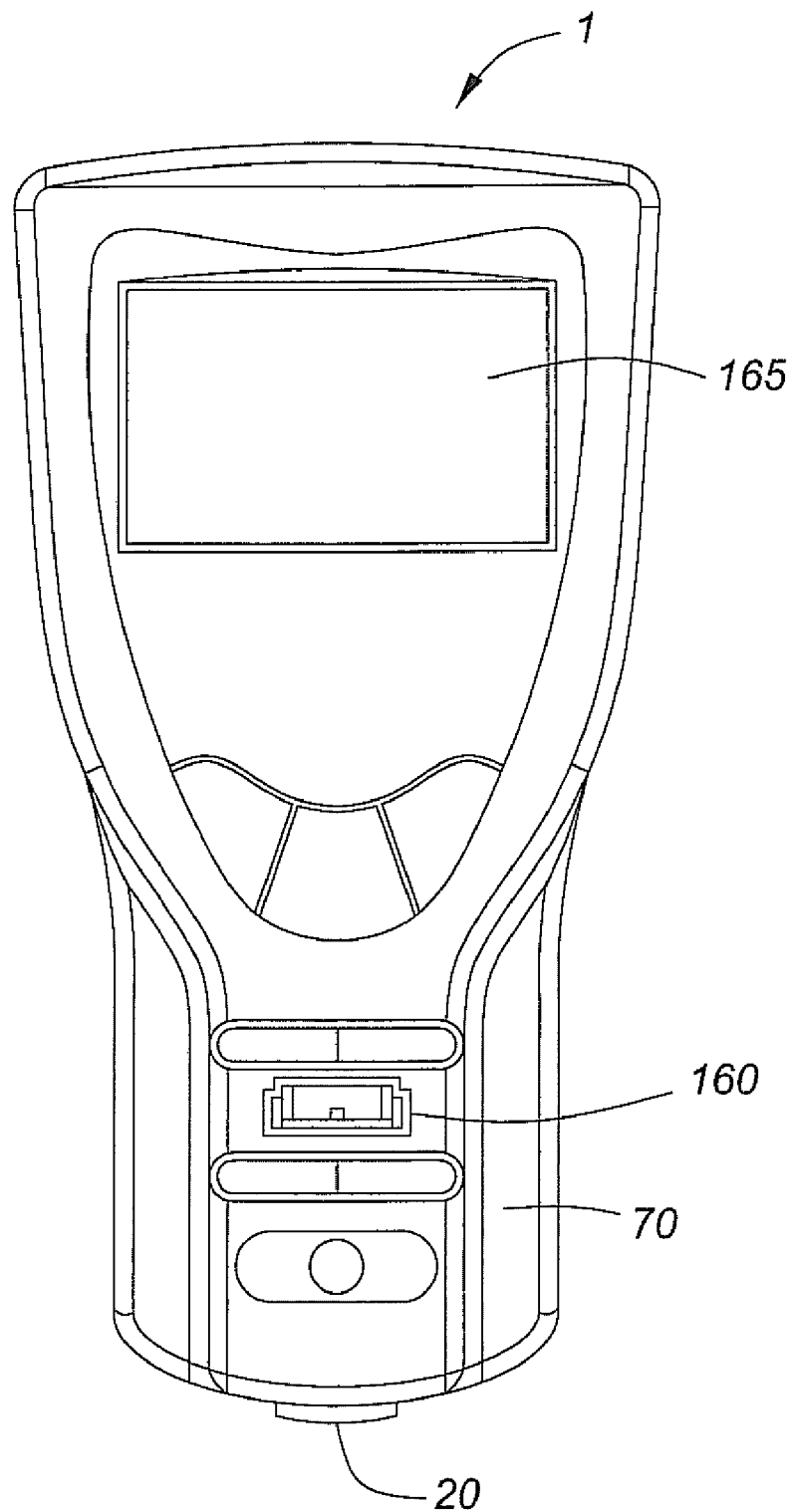
FIG. 4 shows a hand-held device in accordance with a further embodiment of the present invention.
Figure 5:
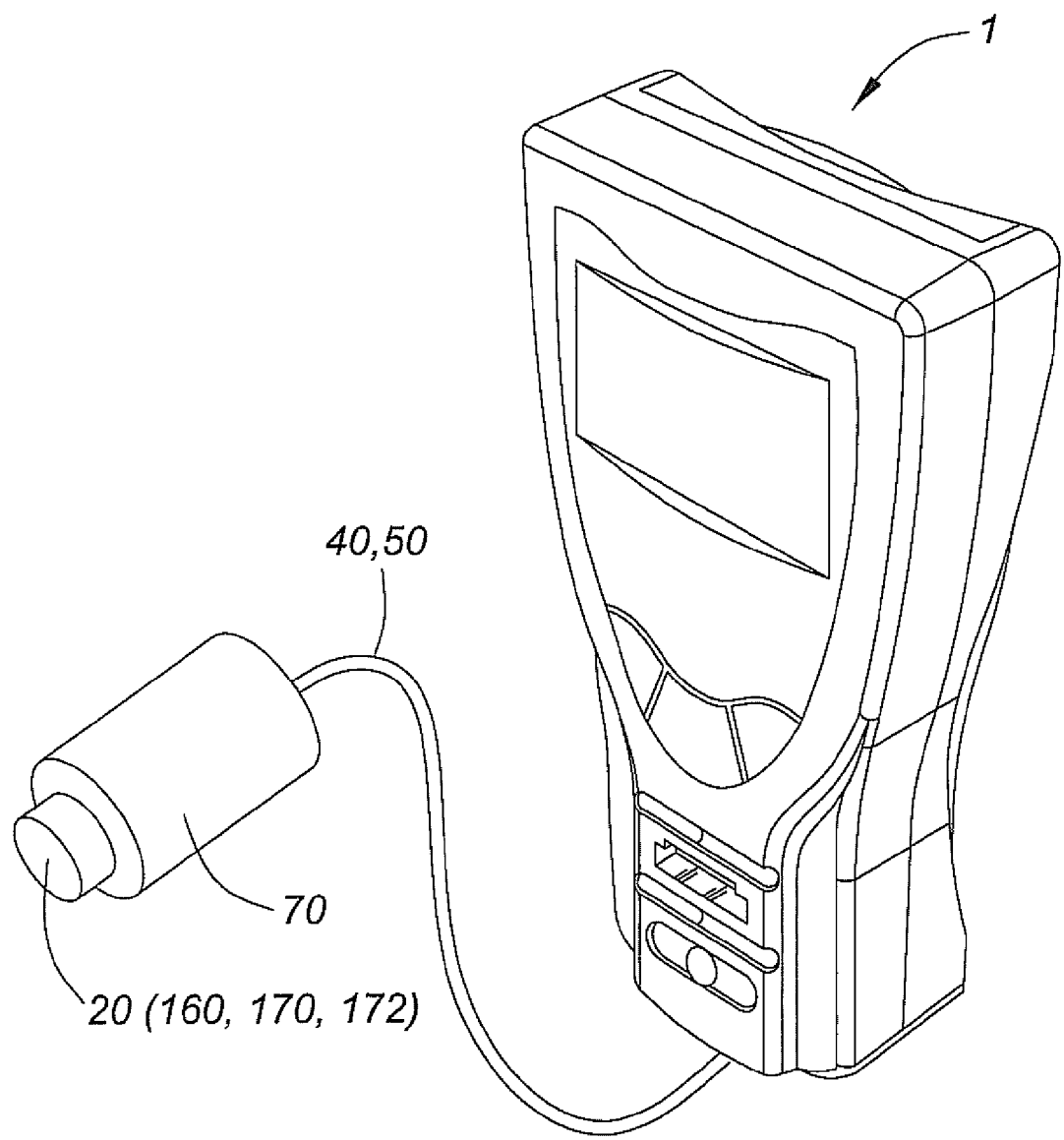
FIG. 5 shows a hand held device with a detachable probe in accordance with a further embodiment of the present invention.

In an alternative embodiment of the present invention, the receptor may also comprise a device for lancing the body part (120, FIG. 2). In this embodiment, the body part is placed under or within the receptor, and the device for lancing the body part is used to prick or lance the skin in order to produce a sample (80). The lancing device may targeted to a location on the body part via a guide (130). In this manner, if required, the sample produce as a result of the lancing device is positioned within the path of the EMR within the receptor (FIG. 2).

In another alternative embodiment, the holder (70) may also receive a suitable sized sample holder, for example a slide well (U.S. Pat. No. 4,387,972, Valencia; U.S. Pat. No. 5,800,781, Gavin et al.; U.S. Pat. No. 5,207,984, Kheiri), a sample tab (e.g. WO 00/70350, Samsoondar), a capillary tube (e.g. U.S. Pat. No. 4,791,938 which is incorporated herein by reference), or a filter paper strip or the like. The sample holder may be introduced within the holder (70) of the device of the present invention to determine the concentration of the sample. In this embodiment, the lid of the sample tab, or slide well is transparent or comprises transparent portions to permit the entry and exit of EMR to interact with the sample. As noted above, the receptor (e.g. 172) may be configured to receive both a body part sample (170) and a sample placed within a sample holder (175), for example as shown in FIGS. 8 and 9.

The reflected, transmitted, or both, EMR following interaction with the sample is collected by using any suitable method, for example, fiber optics, or one or more lenses (e.g. 90, 100), and the output signal (50) directed to a diffraction device that separates the wavelengths of light within the output signal into their component parts. Examples of a diffraction device include but are not limited to a diffraction grating or a holographic grating. The diffracting device preferably disperses the EMR into its component wavelengths so that the dispersed EMR falls along the length of a detector such as, but not limited to a linear array detector (e.g. a 256 element photo diode array), or a CCD. In the case of an array, the detector has a series of diodes and is preferably electronically scanned by a microprocessor to measure the charge accumulated on each diode, the charge being proportional to the intensity of EMR for each wavelength transmitted through or reflected from the part of the subject in the receptor.

The detector is connected to the microprocessor, producing an output spectrum, with the microprocessor analyzing the measurements and ultimately producing a result for each concentration level determined. The processing may comprise one or more than one calibration algorithm (for example as disclosed in U.S. Pat. No. 6,651,015, Samsoondar, which is incorporated herein by reference) that is used to determine a property of one or more than one compound within the sample (80). The result can be stored, shown on a display, or printed on a printer. A keyboard may also be used to allow a user to control the device, for example, to specify a particular constituent to be measured. The timing and control may be activated by a microprocessor to control the device, for example, to determine number and timing of measurements.

If required, the device (1) may also have a second path of EMR (57, FIG. 6) comprising an input (45) and output (47) path that enters the receptor. The second path of EMR interacts with the body part (60) at a location (85) separate from that of the path of EMR that interacts with the sample (80). The second path of EMR (57) is also in operative association with the source of EMR (10), or it may be in operative association with a second source of EMR. The second path of EMR may be used to control for background signals within the receptor (20) and body part (60), or it may be used to determine the concentration of a compound within the body part in a non-invasive manner, for example as described in U.S. Pat. No. 5,361,758 (Hall) or U.S. Pat. No. 6,741,876 (Seciena et al., both of which are incorporated herein by reference).

Therefore, the present invention provides a device for measuring one or more than one compound in a sample, comprising:

a source of electromagnetic radiation (EMR) that emits one or more than one wavelength of EMR, the source of EMR being operatively coupled to a power source;

a holder for receiving a detachable receptor, the holder comprising one or more than one input in operable association with the source of EMR, one or more than one output in operable association with a detector, the one or more than one input and the one or more than output of the holder in optical alignment with one or more than one port located within the receptor, the one or more than one input and the one or more than output defining an EMR path through the holder and within the receptor, wherein, the sample when received by the receptor is placed within the EMR path;

the detector for measuring transmitted or reflected EMR received from the sample, the detector operatively coupled to a processing system;

the processing system comprising one, or more than one calibration algorithm for determining a concentration for the one or more than one compound.

The present invention also provides a device for measuring one or more than one compound in a sample both non-invasively and invasively, comprising:

a source of electromagnetic radiation (EMR) that emits one or more than one wavelength of EMR, the source of EMR being operatively coupled to a power source;

one or more than one receptor for receiving a body part and a sample holder as the sample, the one or more than one receptor optically coupled to the source of EMR by one or more than one radiation guiding element, the radiation guiding element comprising one or more than one input in operable association with the source of EMR, one or more than one output in operable association with a detector, the one or more than one input and the one or more than output in optical alignment with one or more than one port located within the one or more than one receptor, the one or more than one input and the one or more than output defining an EMR path from the no source, through the one or more than one receptor and the detector, wherein the sample when received by the one or more than one receptor is placed within the EMR path;

the detector for measuring transmitted or reflected EMR received from the sample, the detector operatively coupled to a processing system;

the processing system comprising one, or more than one calibration algorithm for determining a concentration for the one or more than one compound.

The device of the present invention may be used to determine the concentration of one or more than one compound, or a percentage of a compound with reference to another compound (i.e. the relative abundance of one compound with respect to another compound) within the sample. The compound may be any compound, and the invention is not meant to be limited by the compound, or compounds, being assayed. For example, which is not to be considered limiting, if the sample is a biological fluid, the compound may be selected from the group consisting of hemoglobin, Oxy-Hb, % oxy-Hb, "Oxy-Hb plus Deoxy-Hb", "Total-Hb minus Met-Hb", Met-Hb, % met-Hb, Carboxy-Hb, % COHb, Sulf-Hb, $HbA_{1c}$, % plasma of a compound (as a percent of the total amount of the compound), % interstitial of a compound (as a percent of the total amount of the compound), cholesterol, glucose, a fat, a protein, a glycoprotein, a lipoprotein, protein C, a carbohydrate (e.g. glucose), plasma glucose, interstitial glucose, % plasma glucose (as a percent of the total amount of glucose), % interstitial glucose (as a percent of the total amount of glucose), a steroid (e.g. cholesterol), an amino acid, nitrogen, carbon dioxide, cortisol, creatine, creatinine, a ketone, a lipid, urea, a fatty acid (such as an omega-3 fatty acid, for example, but not limited to α-linolenic acid, eicosapentaenoic acid, or docosahexaenoic acid; an omega-6 fatty acid, for example, but not limited to linoleic acid, gamma-linolenic acid, eicosadienoic acid, dihomo-gamma-linolenic acid, arachidonic acid, docosadienoic acid, adrenic acid, or docosapentaenoic acid; or an omega-9 fatty acid, for example, but not limited to oleic acid, eicosenoic acid, mead acid, erucic acid or nervonic acid), glycosolated hemoglobin, alcohol, lactate, an ion, $Ca_2^+$, $K^+$, $Cl^-$, $HCO_3^-$ and $HPO_4^-$ and a neutral or ionic form of a heavy metal, or a toxic metal, for example, but not limited to a neutral or ionic form of a metal having an atomic number greater than 20 (calcium), more particularly a metal having an atomic number between 21 (scandium) and 92 (uranium), such as a neutral or ionic form of mercury, arsenic, lead or cadmium.

The processing system of the device of the present invention may be used to determine the oxygen saturation of blood in the part by analyzing the differential absorption of oxygenated hemoglobin, $HbO_2$, and deoxygenated hemoglobin, Hb in arterial blood. Based on the absorbances of the wavelengths of light in the visible red and infrared spectra, the system can calculate a value of arterial oxygen saturation ($Sp_aO_2$) of hemoglobin in the blood of the subject. The system can distinguish hemoglobin absorption from absorption of other components of the tissues within the part based upon the pulsatile nature of arterial blood. In this embodiment, the processing system may further comprise a pulse oximeter.

In a similar manner, the processing system of the device of the present invention may be used to determine the % plasma glucose (as a percent of the total amount of glucose, or as a percentage of the total plasma and interstitial glucose), or % interstitial glucose (as a percent of the total amount of glucose, or as a percentage of the total plasma and interstitial glucose) within a sample by analyzing the differential absorption of plasma glucose and interstitial glucose within a body part. Based on the absorbances of the wavelengths of light in the visible red and infrared spectra, the system can determine a value of % plasma glucose or % interstitial glucose within the subject, or the concentrations of % plasma glucose or % interstitial glucose may be determined.

The concentration of a given compound is preferably calculated according to the present invention by using a calibration equation derived from a statistical analysis, for example but not limited to a least squares best fit, of a plot of the values of concentration of a calibration set of samples of the compound, which are determined using known methods (e.g. U.S. Pat. No. 6,651,015, Samsoondar). However, it is to be understood that other statistical tests may be used was known in the art, for example but not limited to multiple linear regression (MLR), partial least squares (PLS), and the like. Any known method for determining the concentration of one, or more than one, compound may be used as would be known to one of skill in the art. Alternatively, the % value of the one or more than one compound may be determined from predetermined values within a calibration table. The calibration table being determined using a range of given absorption (or transmittance) values and related to % compositions of the compound, so that the absorption (or transmittance) reading is related to a known % of the compound without the need for mathematical manipulation.

As outlined above, the device of the present invention may also include an warning unit, for example an alarm, coupled to the processing system, which produces an signal, for example, an audible, visible or vibrating alarm signal, when the concentration for the compound is outside, at a limit or within a percentage of an upper or a lower limit of a predetermined range of values of concentration for the compound.

For example, in the case where the compound of interest is blood glucose, the alarm signal could be programmed to engage if a measured concentration of blood glucose is indicative of a hyperglycemic state, or a hypoglycemic state, for example but not limited to when the value exceeds 200 gm/ml or falls below 70 gm/ml, respectively. In the case where the alarm is triggered in response to a hyperglycemic state, insulin may then be administered to the patient whose glucose level is being monitored. Conversely, if the alarm goes off in response to a hypoglycemic state, a source of sugar may be provided to the patient.

The present invention also provides a method to determine the concentration of one or more than one compound within the sample and a similar or different compound within the body part that lies along the paths of EMR emitted, and received by, the receptor. In this example, there are two sources of EMR traveling within two paths of EMR. One path of EMR interacts with the sample, for example a drop of blood, while the second path of EMR may interact with the body part in a non-invasive manner, as shown in FIG. 6.

The present invention also provides for a method of determining the concentration of a compound in a sample of blood comprising,
(a) placing a receptor over a portion of a body part, the body part having a sample thereon, the sample may be blood;
(b) directing a source of electromagnetic radiation (EMR) through the receptor and onto the sample;
(c) measuring a quantity of the EMR reflected by, or transmitted through, the sample with a detector; and
(d) performing a quantitative mathematical analysis of the quantity of EMR using an algorithm, and determining the concentration of the compound in the sample.

Prior to the step of placing (step a)), the body part may be pricked or lanced so that the sample is a sample of blood, and the blood is produced on the surface of the body part.

Furthermore, the present invention provides a method of determining the concentration of a compound in a sample of blood comprising,
(a) placing a receptor over a portion of a body part;
(b) lancing the body pair located within the receptor to produce a sample of blood on the surface of the body part,
(b) directing a source of electromagnetic radiation (EMR) through the receptor and onto the sample of blood;
(c) measuring a quantity of the EMR reflected by, or transmitted through, the sample of blood with a detector; and
(d) performing a quantitative mathematical analysis of the quantity of EMR using an algorithm, and determining the concentration of the compound in the sample of blood.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A device for measuring a concentration of a compound in a sample, comprising:
a source of electromagnetic radiation (EMR) that emits one or more than one wavelength of EMR, the source of EMR being operatively coupled to a power source;
a detachable receptor sized to receive the body part;
a holder for receiving the detachable receptor, the holder comprising one or more than one input in operable association with the source of EMR, one or more than one output in operable association with a detector, the one or more than one input and the one or more than one output of the holder in optical alignment with one or more than one port located within the receptor, the one or more than one input and the one or more than output defining an EMR path through the holder and within the receptor, wherein, the sample when received by the receptor is placed within the EMR path;
the detector for measuring transmitted or reflected EMR received from the sample, the detector operatively coupled to a processing system;
the processing system comprising one, or more than one calibration algorithm for determining a concentration for the one or more than one compound, or a calibration table for determining the percent of the one or more than one compound.

2. The device of claim 1, wherein the detachable receptor is sized to fit over a drop of blood located on the body part.

3. The device of claim 1 comprising a second path of EMR through the holder and within the detachable receptor, wherein the second path of EMR interacts with the sample at a location separate from that of the EMR path, the second path of EMR is in operative association with the source of EMR or a second source of EMR.

4. The device of claim 1, wherein the detachable receptor or the holder further comprises an apparatus for lancing a body part when the body part is positioned with the receptor.

5. The device of claim 1 wherein the holder is a probe, the probe being removable from the source of EMR, the detector, or both the source of EMR and detector, and the probe being optically associated with the source of EMR and the detector.

6. The device of claim 1, wherein the receptor comprises a matrix that can wick the sample off a surface of a body part.

7. The device according to claim 1, wherein the compound is selected from the group consisting of hemoglobin, Oxy-Hb, % oxy-Hb, "Oxy-Hb plus Deoxy-Hb", "Total-Hb minus Met-Hb", Met-Hb, % met-Hb, Carboxy-Hb, % CO-Hb, Sulf-Hb, cholesterol, glucose, a fat, a protein, a glycoprotein, a lipoprotein, a carbohydrate, a steroid, an amino acid, nitrogen, carbon dioxide, cortisol, creatine, creatinine, a ketone, a lipid, urea, a fatty acid, glycosolated hemoglobin, alcohol, lactate, an ion, $Ca^{2+}$, $K^+$, $Cl^-$, $HCO_3^-$ and $HPO_4^-$.

8. The device according to claim 1, wherein the source of EMR comprises wavelengths from about 300 nm to about 2500 nm.

9. The device according to claim 1, wherein the source of EMR comprises wavelengths from about 500 nm to about 1100 nm.

10. A method of determining the concentration of a compound in a sample of blood comprising,
(a) placing the receptor of the device defined in claim 1 over a portion of a body part, the body part having a sample of blood thereon,
(b) directing the source of electromagnetic radiation (EMR) of the device through the receptor and onto the sample of blood disposed on the body part;
(c) measuring a quantity of the EMR reflected by, or transmitted through, the sample of blood disposed on the body part with the detector of the device; and
(d) determining a value of the compound in the sample of blood.

11. The method according to claim 10, wherein the compound is selected from the group consisting of a fat, a protein, a glycoprotein, hemoglobin, Oxy-Hb, % oxy-Hb, "Oxy-Hb plus Deoxy-Hb", "Total-Hb minus Met-Hb", Met-Hb, % met-Hb, Carboxy-Hb, Co-Hb, Sulf-Hb, cholesterol, glucose, a fat, a protein, a glycoprotein, a lipoprotein, a carbohydrate, a steroid, an amino acid, nitrogen, carbon dioxide, cortisol, creatine, creatinine, a ketone, a lipid, urea, a fatty acid, glycosolated hemoglobin, alcohol, lactate, an ion, $Ca^{2+}$, $K^+$, $Cl^-$, $HCO_3^-$ and $HPO_4^-$.

12. The method of claim 10, wherein prior to the step of placing (step a)), the body part is lanced so that the sample of blood is produced on the surface of the body part.

13. The method claim 10, wherein prior to the step of placing (step (a)), the receptor is placed within a holder.

14. The method of claim 10, wherein after the step of measuring (step (c)) the receptor is removed from the holder.

15. The method according to claim 10, wherein in the step of measuring (step (b)), the source of EMR comprises wavelengths from about 300 nm to about 2500 nm.

16. The method according to claim 10, wherein in the step of measuring (step (b)), the source of EMR comprises wavelengths from about 500 nm to about 1100 nm.

17. The method of claim 10, wherein in the step of placing (step (a)), the sample is wicked within the receptor.

18. The method of claim 10, wherein in the step of directing (step (b)), a second source of EMR is directed to the body part, and a measurement of background is obtained.

19. The method of claim 10, wherein in the step of directing (step (b)), a second source of EMR is directed to the body part, and in the step of measuring (step (c)), a non-invasive measurement is made of one or more compound within the body part.

20. The device according to claim 1, further comprising an warning unit coupled to the processing system, the warning unit producing a signal when the concentration for the compound is outside or at a limit of a predetermined range of values of concentration for the compound.

21. A device for measuring one or more than one compound in a sample both non-invasively and invasively, comprising:
   a source of electromagnetic radiation (EMR) that emits one or more than one wavelength of EMR, the source of EMR being operatively coupled to a power source;
   one or more than one receptor adapted to receive a body part and a sample holder as the sample, the one or more than one receptor optically coupled to the source of EMR by one or more than one radiation guiding element, the radiation guiding element comprising one or more than one input in operable association with the source of EMR, one or more than one output in operable association with a detector, the one or more than one input and the one or more than output in optical alignment with one or more than one port located within the one or more than one receptor, the one or more than one input and the one or more than output defining an EMR path from the source, through the one or more than one receptor and the detector, wherein, the sample when received by the one or more than one receptor is placed within the EMR path;
   the detector for measuring transmitted or reflected EMR received from the sample, the detector operatively coupled to a processing system;
   the processing system comprising one, or more than one calibration algorithm for determining a concentration for the one or more than one compound, or a calibration table for determining the percent of the one or more than one compound.

22. The device according to claim 21, wherein the one or more than on receptor comprises a first receptor for receiving a body part, and a second receptor for receiving a sample holder.

23. The device according to claim 21, wherein the one or more than on receptor comprises one receptor, the one receptor for receiving a body part, and an insert, the insert for receiving a sample holder.

24. The device according to claim 21, further comprising a warning unit coupled to the processing system, the warning unit producing a signal when the concentration for the compound is outside or at a limit of a predetermined range of values of concentration for the compound.

25. A method of determining the concentration of a compound in blood within a body part comprising,
   (a) determining when the concentration for the compound measured using a non-invasive method is outside or at a limit of a predetermined range of values of concentration;
   (b) placing a receptor over a portion of a body part, the body part having a sample of blood thereon,
   (c) directing a source of electromagnetic radiation (EMR) through the receptor and onto the sample of blood;
   (d) measuring a quantity of the EMR reflected by, or transmitted through, the sample of blood with a detector; and
   (e) performing a quantitative mathematical analysis of the quantity of EMR using an algorithm, and determining the concentration of the compound in the sample of blood.

26. The method of claim 25, wherein the step of determining (step (a)) comprises detecting an alarm signal produced by a non-invasive device used to measure the concentration of the compound in the non-invasive method.

27. The method of claim 25, wherein the compound is selected from the group consisting of a fat, a protein, a glycoprotein, hemoglobin, Oxy-Hb, % oxy-Hb, "Oxy-Hb plus Deoxy-Hb", "Total-Hb minus Met-Hb", Met-Hb, % met-Hb, Carboxy-Hb, Co-Hb, Sulf-Hb, cholesterol, glucose, plasma glucose, interstitial glucose, % plasma glucose, % interstitial glucose, a fat, a protein, a glycoprotein, a lipoprotein, a carbohydrate, a steroid, an amino acid, nitrogen, carbon dioxide, cortisol, creatine, creatinine, a ketone, a lipid, urea, a fatty acid, glycosolated hemoglobin, alcohol, lactate, an ion, $Ca^{2+}$, $K^+$, $Cl^-$, $HCO_3^-$ and $HPO_4^-$.

* * * * *